US012688613B2

(12) United States Patent
Brown et al.

(10) Patent No.: US 12,688,613 B2
(45) Date of Patent: Jul. 21, 2026

(54) IMAGING CHAMBER FOR AN IMAGING SYSTEM

(71) Applicant: Honeywell International Inc., Charlotte, NC (US)

(72) Inventors: Andy Walker Brown, Richardson, TX (US); Ronald W. Myers, Dublin, OH (US); Daniel Yee, Fort Mill, SC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 447 days.

(21) Appl. No.: 18/176,883

(22) Filed: Mar. 1, 2023

(65) Prior Publication Data

US 2024/0296589 A1     Sep. 5, 2024

(51) Int. Cl.
*G06T 7/90* (2017.01)
*A61B 6/00* (2024.01)
*G06T 7/00* (2017.01)

(52) U.S. Cl.
CPC .............. *G06T 7/90* (2017.01); *A61B 6/5217* (2013.01); *G06T 7/0012* (2013.01); *G06T 2207/30104* (2013.01)

(58) Field of Classification Search
CPC ..................... G06T 7/90; G06T 7/0012; G06T 2207/30104; A61B 6/5217; A61B 5/6866; A61B 10/007; A61B 5/14546; A61B 5/1455; A61B 5/14507; A61M 1/28; A61M 5/007; G01N 15/1436; G01N 15/1484; G01N 2015/016; G01N 2015/1486
See application file for complete search history.

(56) References Cited

U.S. PATENT DOCUMENTS

| | | | |
|---|---|---|---|
| 5,895,762 A | | 4/1999 | Greenfield et al. |
| 6,317,623 B1 | | 11/2001 | Griffiths et al. |
| 7,351,221 B2 | * | 4/2008 | Trombley, III ......... B01F 29/81 |
| | | | 604/82 |
| 9,682,375 B2 | * | 6/2017 | Bransky ............... B01L 3/5027 |
| 9,814,827 B2 | * | 11/2017 | Uber, III ............. A61M 5/1407 |
| 2006/0263888 A1 | | 11/2006 | Fritz et al. |
| 2008/0100840 A1 | | 5/2008 | Oma et al. |
| 2021/0039093 A1 | | 2/2021 | Jones et al. |
| 2022/0011722 A1 | * | 1/2022 | Gusyatin ........... G01N 15/1433 |
| 2022/0074845 A1 | * | 3/2022 | Muzykovski ...... G01N 33/5302 |

FOREIGN PATENT DOCUMENTS

| | | | | |
|---|---|---|---|---|
| EP | 1966587 B1 | | 7/2018 | |
| WO | WO-2020141463 A2 | * | 7/2020 | ............. G06V 20/69 |
| WO | WO-2022005397 A1 | * | 1/2022 | ......... A61B 5/14532 |
| WO | WO-2022165270 A1 | * | 8/2022 | .......... A61B 5/6866 |

OTHER PUBLICATIONS

Extended European Search Report Mailed on Oct. 10, 2024 for EP Application No. 24154918, 18 page(s).
Partial European search report Mailed on Jul. 18, 2024 for EP Application No. 24154918, 19 page(s).

* cited by examiner

*Primary Examiner* — Shefali D Goradia
(74) *Attorney, Agent, or Firm* — Alston & Bird LLP

(57) ABSTRACT

An imaging chamber configured to receive a flow of a fluid sample is provided. The imaging chamber includes a reservoir and an imaging window. The reservoir includes a contrast-enhancing agent and is configured to receive the flow of the fluid sample. The imaging window of the imaging chamber is downstream from the reservoir.

17 Claims, 7 Drawing Sheets

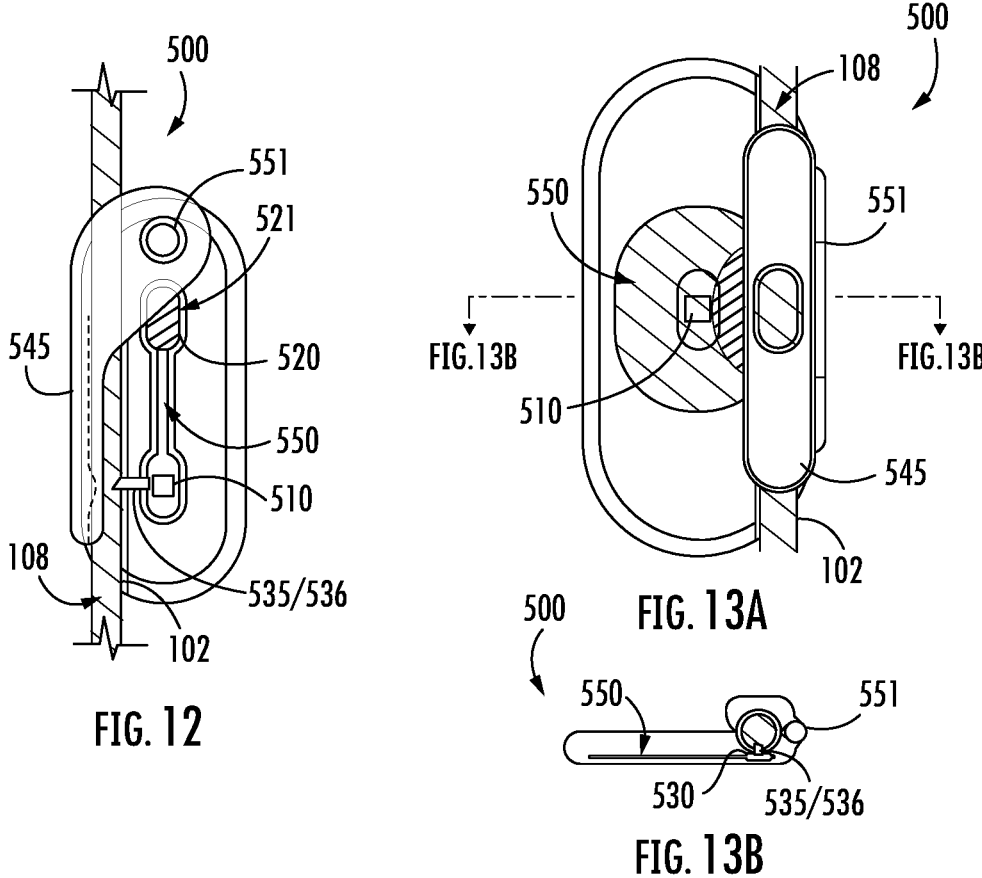
FIG. 12
FIG. 13A
FIG. 13B
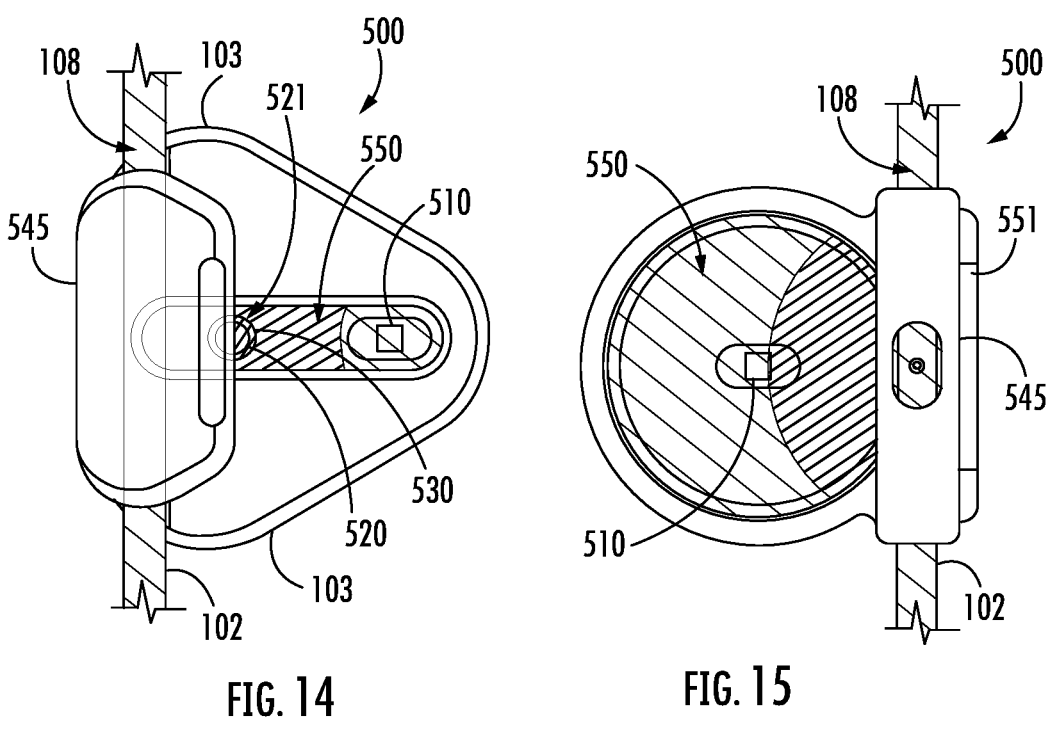
FIG. 14
FIG. 15

900

910

RECEIVING A FLUID SAMPLE THAT COMPRISES BIOLOGICAL CELLS INTO AN IMAGING CHAMBER, WHEREIN THE IMAGING CHAMBER COMPRISES A CONTRAST-ENHANCING AGENT

920

MIXING THE FLUID SAMPLE WITH THE CONTRAST-ENHANCING AGENT TO FORM THE FLUID MIXTURE

930

IMAGING THE FLUID MIXTURE THAT IS WITHIN THE IMAGING CHAMBER WITH THE IMAGING SYSTEM

IMAGING CHAMBER FOR AN IMAGING SYSTEM

TECHNICAL FIELD

Example embodiments of the present disclosure relate generally to an imaging chamber for imaging a fluid sample. More specifically, example embodiments of the present disclosure relate to an imaging chamber that is configured to allow a fluid sample to mix with a contrast-enhancing agent, forming a fluid mixture. The fluid mixture within the imaging chamber can subsequently be imaged by an imaging system (e.g., a digital holography image device).

BACKGROUND

Fluid samples from patients (e.g., blood, urine, or peritoneal dialysis effluent) are often mixed with a contrast-enhancing agent to facilitate the differentiation of particles or cells within the fluid sample when the sample is imaged (e.g., imaged by a digital holography image device). The image data of the fluid mixture is often analyzed for identification and classification of white blood cells to determine whether a patient has an infection.

However, conventional methods of mixing the contrast-enhancing agent with the fluid sample can be time consuming and require certain expertise because it often involves iterative 'fixing', staining, and rinsing steps. This deficiency becomes even more problematic when the fluid sample is being handled and imaged by an individual that is unskilled in using contrast-enhancing agents.

For example, peritoneal dialysis (PD) is often performed outside of a clinic and at a patient's home. It may be beneficial to collect the image data of the PD effluent within a relatively short time frame from when the fluid flows out of the patient's body. For example, it may be more beneficial for the image data of the PD effluent to be generated at the patient's home instead of delivering the fluid sample to a lab or a clinic for analysis. Because patients, in general, can be unskilled at mixing the contrast-enhancing agent with the fluid sample, the iterative fixing, staining, and rinsing steps of conventional methods may not have desired results. Through applied effort, ingenuity, and innovation, many of these identified deficiencies and problems have been solved by developing solutions that are structured in accordance with the embodiments of the present disclosure, many examples of which are described in detail herein.

BRIEF SUMMARY

In general, embodiments of the present disclosure provided herein include methods and apparatuses to provide for an improved imaging chamber.

In various aspects, an imaging chamber configured to receive a flow of a fluid sample is provided. The imaging chamber can include a reservoir and an imaging window. The reservoir can include a contrast-enhancing agent and can be configured to receive the flow of the fluid sample. The imaging window can be in fluid communication with the reservoir and downstream from the reservoir.

In various examples, the imaging window is optically clear. The imaging chamber can be configured to be imaged by an imaging system that includes an illumination device and an imaging device.

In various examples, the imaging chamber includes a mixing device that is upstream from the imaging window.

In various examples, the imaging chamber includes a flow restriction device that is configured to be in an open position and in a closed position, wherein the flow restriction device is configured to allow a flow of the fluid sample and/or a flow of the contrast-enhancing agent to flow through and/or past the flow restriction device when the flow restriction device is in the open position, and wherein the flow restriction device is configured to prevent the flow of the fluid sample and/or the flow of the contrast-enhancing agent to flow through and/or past the flow restriction device when the flow restriction device is in the closed position.

In various examples, the imaging chamber includes an encapsulation. The contrast-enhancing agent can be encapsulated within the encapsulation of the imaging chamber. The imaging chamber can include a seal-breaking mechanism that is configured to break the encapsulation of the imaging chamber. The seal-breaking mechanism can be configured to puncture a tube that comprises the flow of the fluid sample.

In various examples, the fluid sample is a peritoneal dialysis (PD) effluent.

In various examples, the imaging chamber includes a puncturing mechanism that is configured to pierce a drainage bag or tube. The imaging chamber can receive the flow of the fluid sample through the puncturing mechanism.

In various aspects, an imaging system is configured to receive an imaging chamber. The imaging system can include an illumination device and an imaging device. The imaging system can be configured to receive the imaging chamber between the illumination device and the imaging device. The imaging chamber can include a reservoir comprising a contrast-enhancing agent, the reservoir configured to receive a flow of a fluid sample. The imaging chamber can include an imaging window in fluid communication with the reservoir and downstream from the reservoir. The imaging device can be configured to be aligned with the imaging window of the imaging chamber.

In various examples, the imaging system includes an agitation device that is configured to agitate or shake the imaging chamber.

In various examples, the imaging system is configured to receive the flow of the fluid sample and the imaging chamber is configured to be within the imaging system when it receives the flow of the fluid sample.

In various aspects, a method for imaging a fluid mixture with an imaging system includes receiving a fluid sample that includes biological cells into an imaging chamber. The imaging chamber can include a contrast-enhancing agent. The method can include mixing the fluid sample with the contrast-enhancing agent to form the fluid mixture and imaging the fluid mixture that is within the imaging chamber with the imaging system.

In various examples, receiving the fluid sample includes receiving the fluid sample from a bag or tube.

In various examples, the method includes opening a flow restriction device of the imaging chamber.

In various examples, mixing the fluid sample with the contrast-enhancing agent includes mixing the fluid sample with the contrast-enhancing agent with a mixing device.

In various examples, the fluid sample comprises a PD effluent.

In various examples, the imaging system comprises a digital holography imaging device.

In various examples, mixing the fluid sample with the contrast-enhancing agent is performed by hand outside of the imaging system.

In various examples, mixing the fluid sample with the contrast-enhancing agent is performed inside the imaging system by an agitation device of the imaging system.

The above summary is provided merely for purposes of summarizing some example embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses many potential embodiments in addition to those here summarized, some of which will be further described below. Other features, aspects, and advantages of the subject matter will become apparent from the description, the drawings, and the claims.

BRIEF DESCRIPTION OF THE DRAWINGS

Figure 1A:
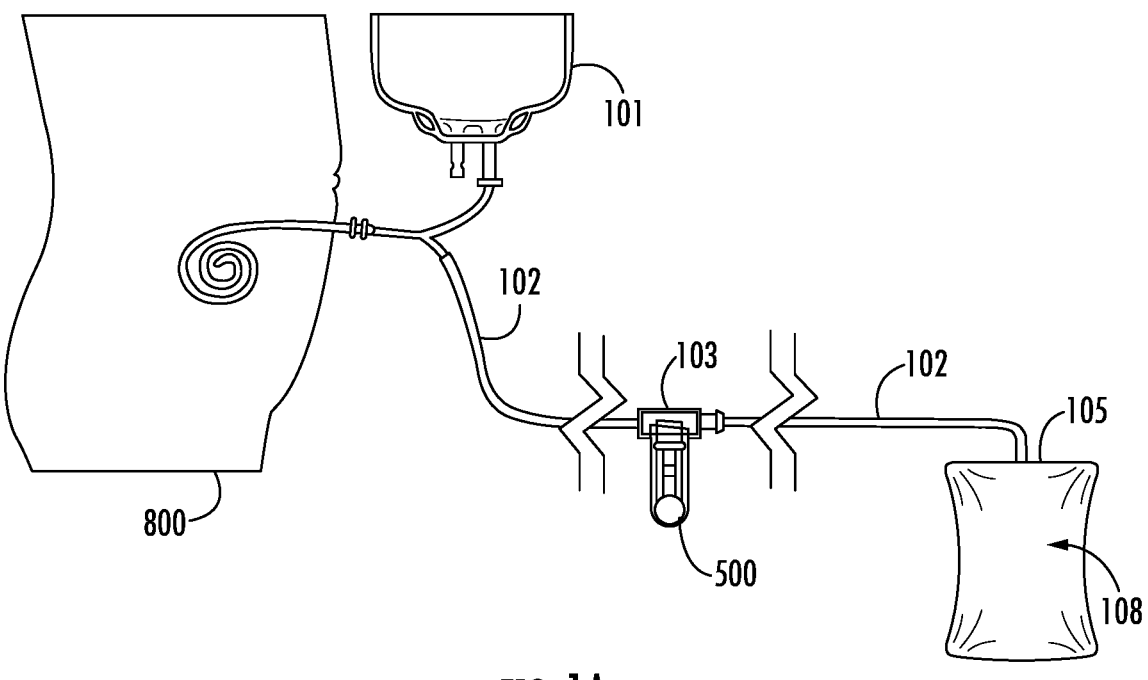

Having thus described certain example embodiments of the present disclosure in general terms above, non-limiting and non-exhaustive embodiments of the subject disclosure are described with reference to the following figures, which are not necessarily drawn to scale and wherein like reference numerals refer to like parts throughout the various views unless otherwise specified. The components illustrated in the figures may or may not be present in certain embodiments described herein. Some embodiments may include fewer (or more) components than those shown in the figures.

Figure 1B:
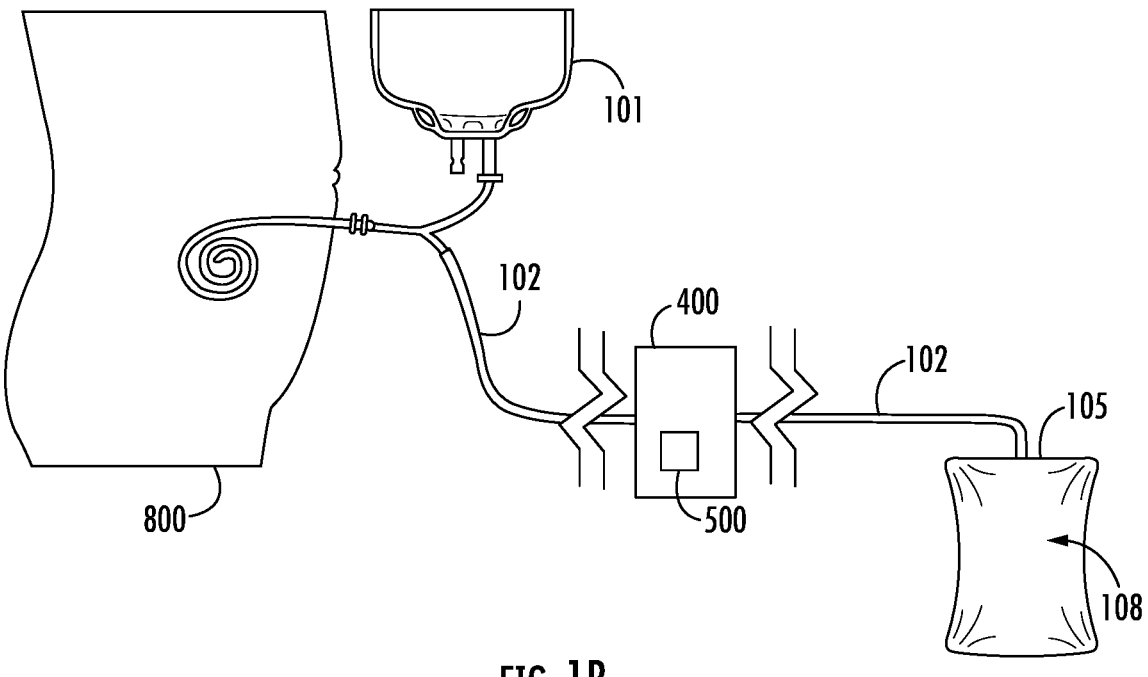
Figure 1C:
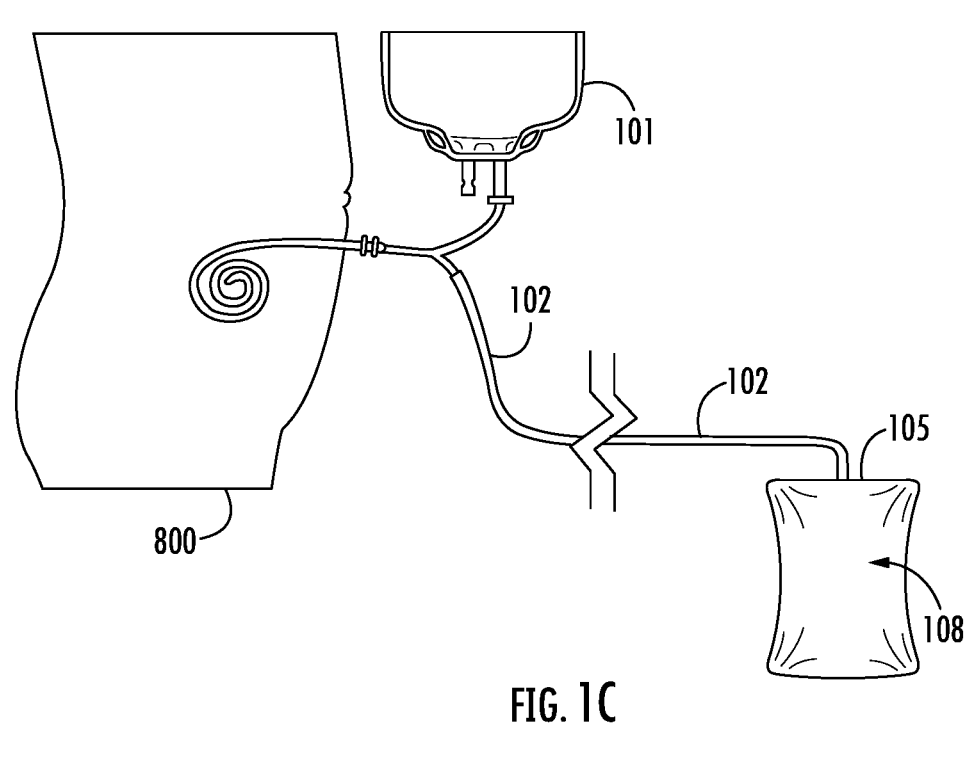

FIGS. 1A-1C provide a schematic depiction of a patient undergoing a peritoneal dialysis procedure, according to example embodiments.

Figures 2A, 2B, 2C:
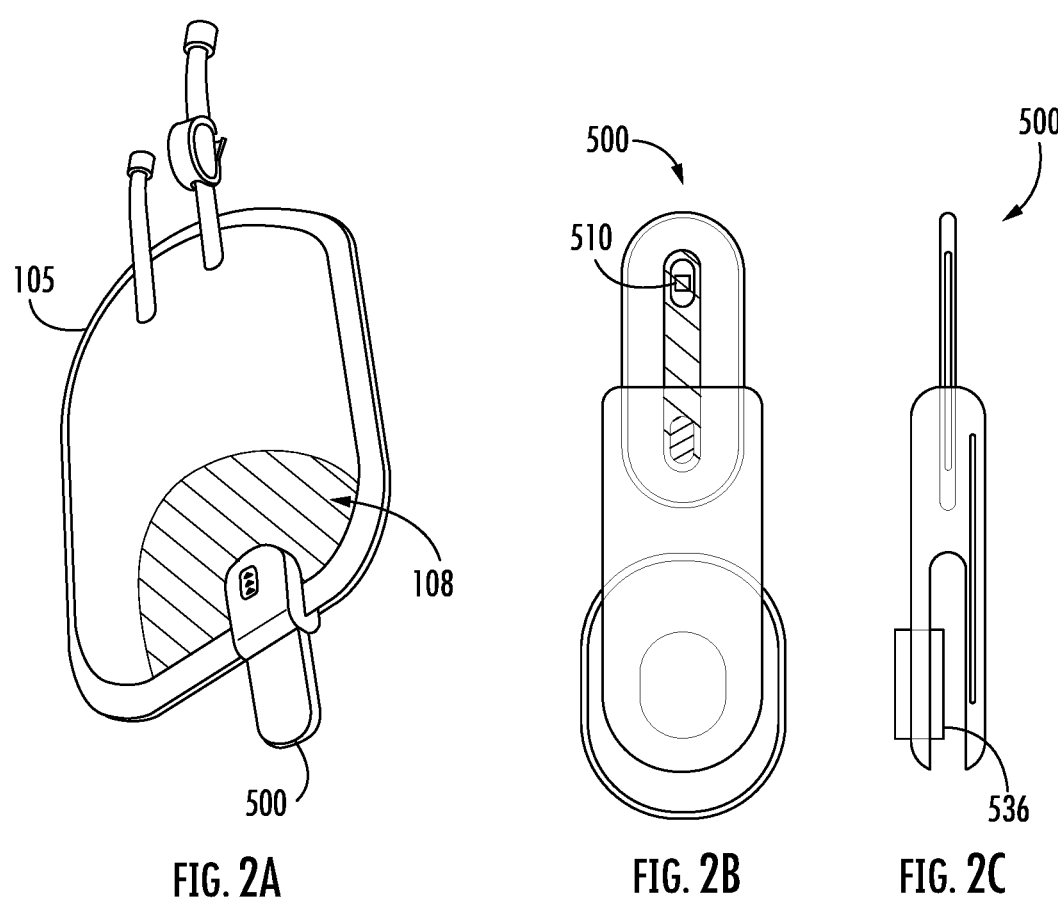

FIG. 2A provides a perspective view of an imaging chamber clamped to a drainage bag, according to an example embodiment.

FIG. 2B provides a top view of the imaging chamber of FIG. 2A, according to an example embodiment.

FIG. 2C provides a side view of the imaging chamber of FIG. 2A, according to an example embodiment.

Figures 3A, 3B, 3C:
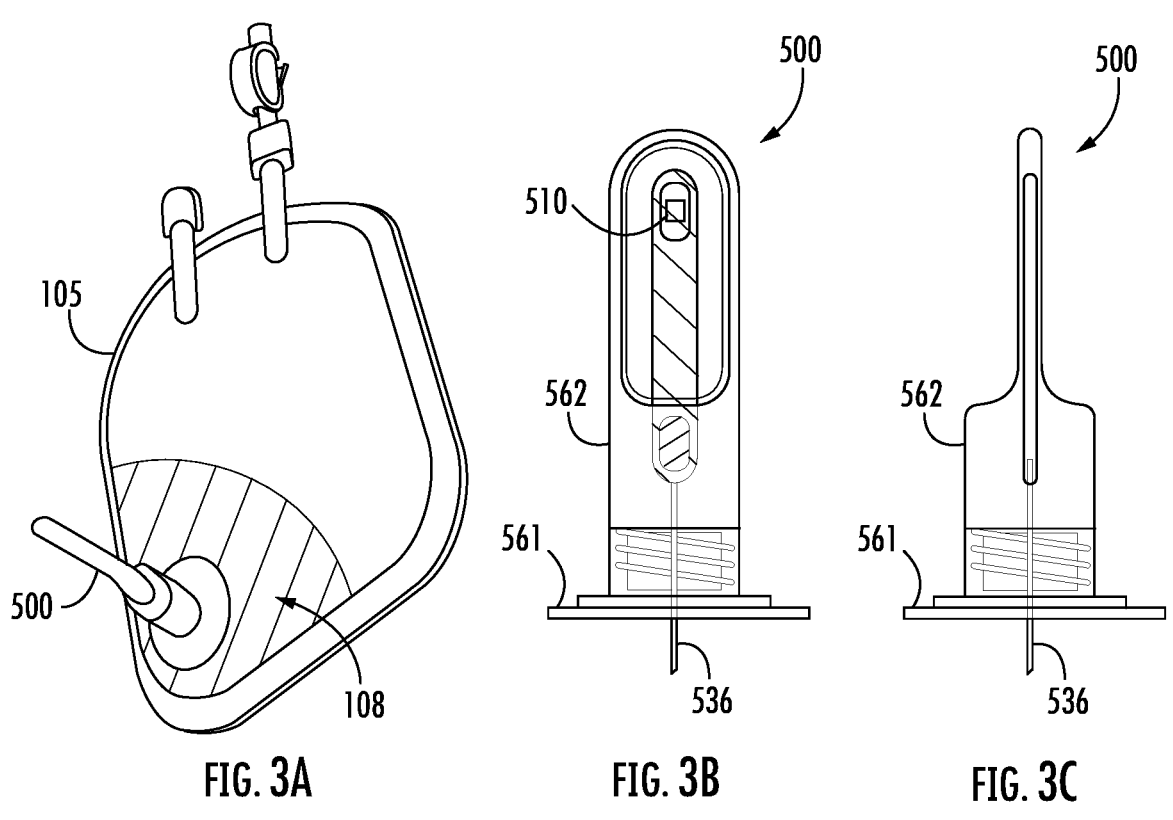

FIG. 3A provides a perspective view of an imaging chamber clamped to a drainage bag, according to an example embodiment.

FIG. 3B provides a top view of the imaging chamber of FIG. 2A, according to an example embodiment.

FIG. 3C provides a side view of the imaging chamber of FIG. 2A, according to an example embodiment.

FIGS. 4-10 provide top views of imaging chambers, according to example embodiments.

Figures 7, 8, 9, 10, 11A, 11B:
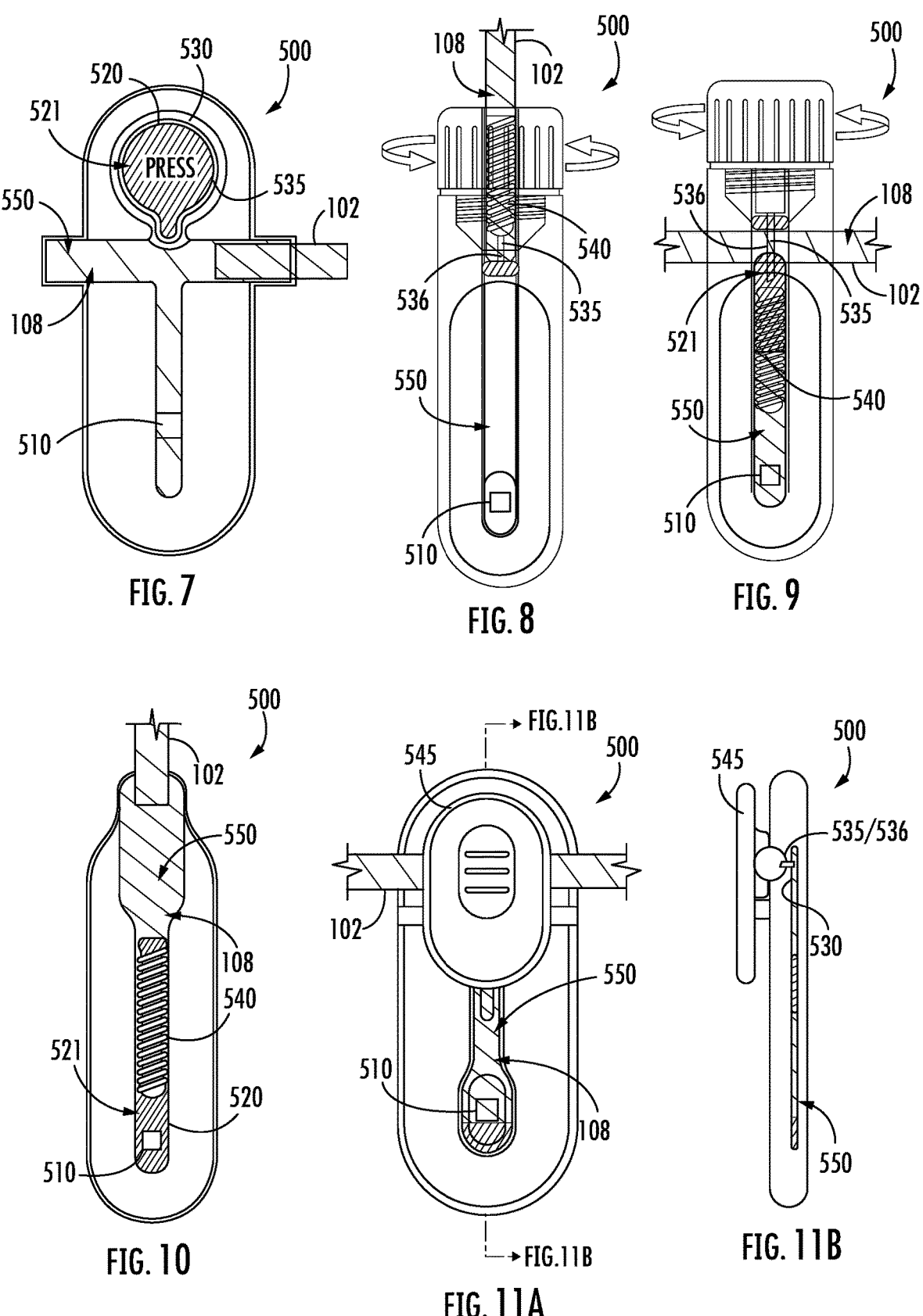

FIG. 11A provides a top view of an imaging chamber, according to an example embodiment.

FIG. 11B provides a side view of the imaging chamber of FIG. 11A, according to an example embodiment.

FIG. 12 provides a top view of an imaging chamber, according to an example embodiment.

FIG. 13A provides a top view of an imaging chamber, according to an example embodiment.

FIG. 13B provides a side view of the imaging chamber of FIG. 13A, according to an example embodiment.

Figure 16:
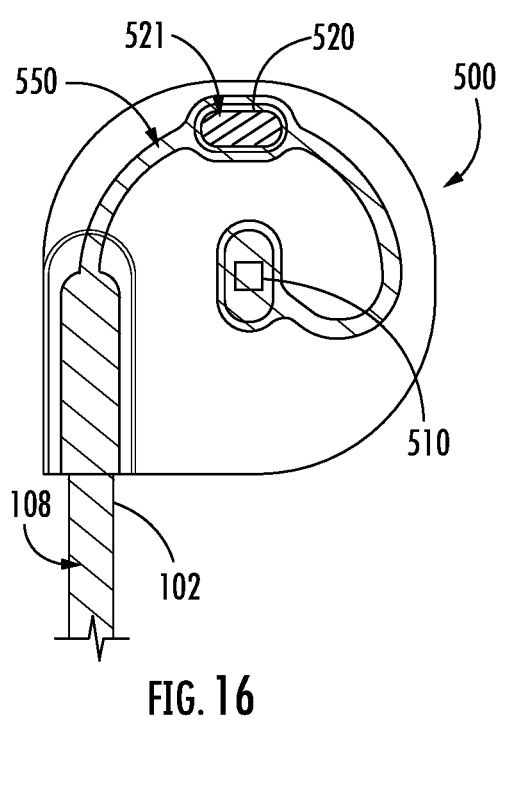

FIGS. 14-16 provide top views of imaging chambers, according to example embodiments.

Figure 17:
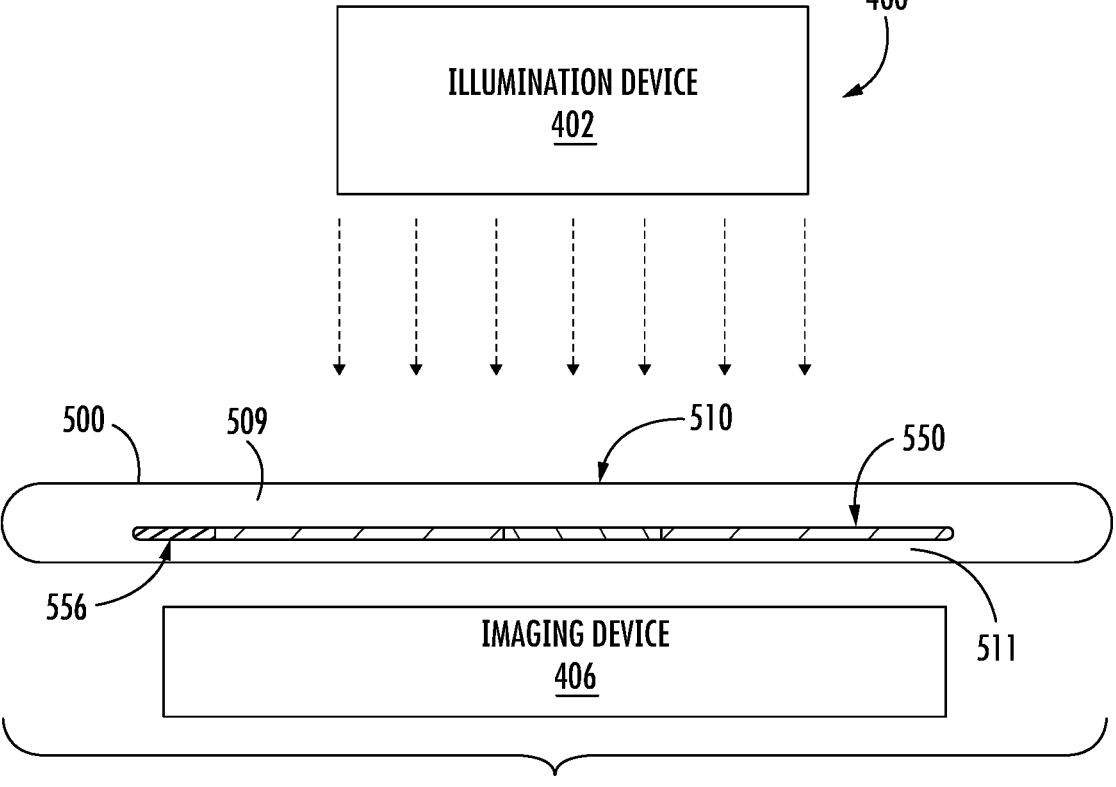

FIG. 17 provides a schematic, side view of an imaging system, according to an example embodiment.

Figure 18:
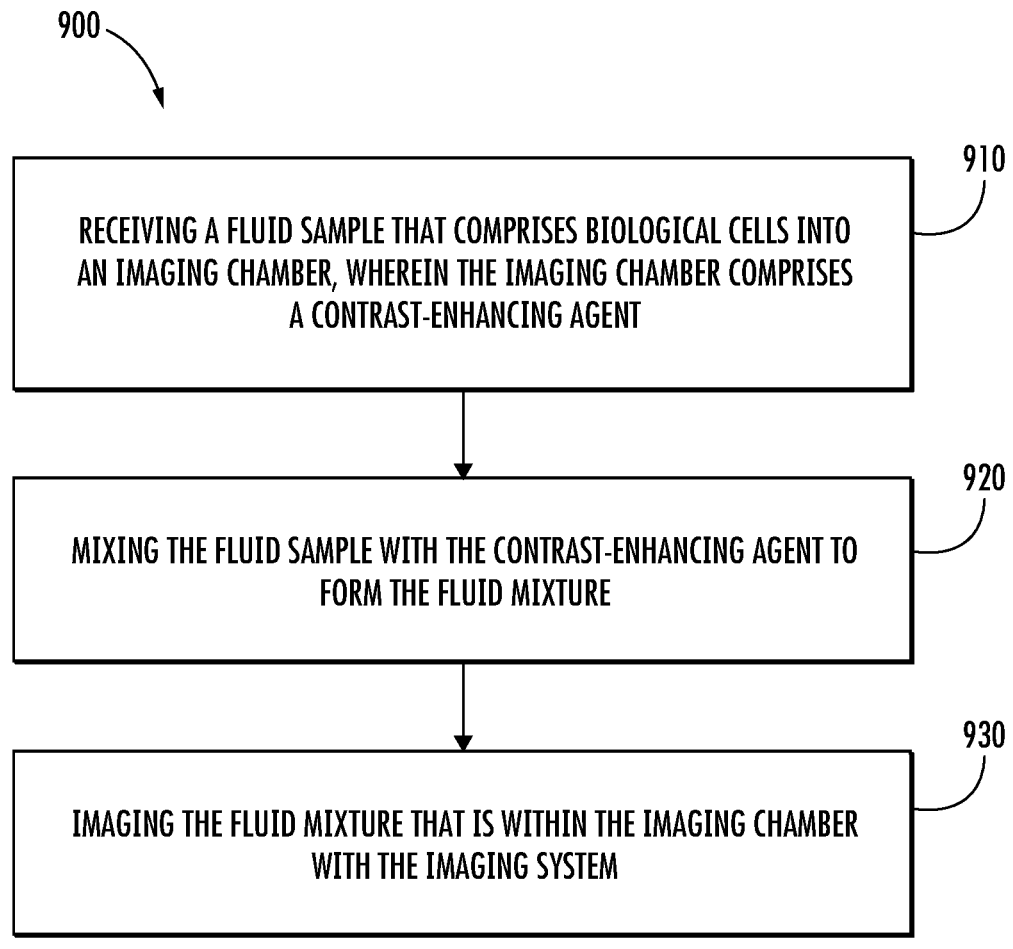

FIG. 18 provides a flowchart of a method for imaging a fluid mixture within an imaging system, according to an example embodiment.

DETAILED DESCRIPTION

One or more embodiments are now more fully described with reference to the accompanying drawings, wherein like reference numerals are used to refer to like elements throughout and in which some, but not all embodiments of the inventions are shown. In the following description, for purposes of explanation, numerous specific details are set forth in order to provide a thorough understanding of the various embodiments. It is evident, however, that the various embodiments can be practiced without these specific details. It should be understood that some, but not all embodiments are shown and described herein. Indeed, the embodiments may be embodied in many different forms, and accordingly this disclosure should not be construed as limited to the embodiments set forth herein. Rather, these embodiments are provided so that this disclosure will satisfy applicable legal requirements.

As used herein, the term "exemplary" means serving as an example, instance, or illustration. Any aspect or design described herein as "exemplary" is not necessarily to be construed as preferred or advantageous over other aspects or designs. Rather, use of the word exemplary is intended to present concepts in a concrete fashion. In addition, while a particular feature may be disclosed with respect to only one of several implementations, such feature may be combined with one or more other features of the other implementations as may be desired and advantageous for any given or particular application. Furthermore, to the extent that the terms "includes" and "including" and variants thereof are used in either the detailed description or the claims, these terms are intended to be inclusive in a manner similar to the term "comprising."

As used herein, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As used herein, the terms "upstream" and "downstream" refer to the relative direction with respect to fluid flow in a fluid pathway. For example, "upstream" refers to the direction from which the fluid flows, and "downstream" refers to the direction to which the fluid flows. As used herein, the term "fluid communication" means that a fluid is capable of making the connection between the areas specified.

As used herein, the terms "coupled," "fixed," "attached to," and the like refer to both direct coupling, fixing, or attaching, as well as indirect coupling, fixing, or attaching through one or more intermediate components or features, unless otherwise specified herein.

As used herein, the term "positioned directly on" refers to a first component being positioned on a second component such that they make contact. Similarly, as used herein, the term "positioned directly between" refers to a first component being positioned between a second component and a third component such that the first component makes contact with both the second component and the third component. In contrast, a first component that is "positioned between" a second component and a third component may or may not have contact with the second component and the third component. Additionally, a first component that is "positioned between" a second component and a third component is positioned such that there may be other intervening components between the second component and the third component other than the first component.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

Referring now to FIGS. 1A-1C, a patient 800 undergoing a peritoneal dialysis (PD) procedure is schematically depicted, according to an example embodiment. The PD procedure provides a mechanism to remove waste products from a patient's blood when the patient's kidneys cannot adequately function. During an example PD procedure, a cleansing fluid (such as, but not limited to, a dialysis solution such as water with sugar and other additives) flows from a treatment solution bag 101, through a tube or a pipe (such as, but not limited to, a catheter), and into the patient's body 800. More specifically, the cleansing fluid is injected into a part of a patient's abdomen. When the cleansing fluid is inside the patient's body 800, the cleansing fluid absorbs waste products from the patient's body 800. The lining of the abdomen (also known as peritoneum) can act as a filter and remove waste products from the patient's blood. After a set period of time, the fluid with the filtered waste products (referred herein as peritoneal dialysis (PD) effluent) flows out of the patient's abdomen.

PD procedures may be faced with some drawbacks. One of the drawbacks is that patients who undergo PD may develop infections. As such, early detection of infections after a patient undergoes PD can be beneficial for alerting patients, as well as care providers, so that early action can be taken to limit the severity and frequency of infections. Various embodiments of the present disclosures may enable such early detection of infections while a patient undergoes PD.

As will be discussed further, various embodiments of the present disclosures provide an imaging system 400 (FIG. 17) that provides a mechanism to sample PD effluent and capture image data associated with the PD effluent. In various examples, a contrast-enhancing agent 521 is mixed with the fluid sample 108, such as the PD effluent, to form a fluid mixture 556. The fluid mixture 556 can then be imaged by the imaging system 400 and the images captured by the imaging system 400 can be analyzed to count, identify, and/or classify particles and/or cells in the fluid mixture 556. As will be appreciated, certain types or quantities of particles or cells, such as white blood cells, may indicate that the patient may have, or may be developing, an infection. As will also be appreciated, the fluid mixture 556, which is a mixture of the fluid sample 108 and the contrast-enhancing agent 521, may be easier to analyze than the fluid sample 108 without the contrast-enhancing agent 521. However, conventional methods of mixing the contrast-enhancing agent 521 with a fluid sample 108 can be manual, time consuming, and may require certain expertise to successfully stain the particles and cells within the fluid sample 108. As such, new methods and apparatuses to prepare a fluid mixture 556 of a fluid sample 108 and a contrast-enhancing agent 521 would be welcomed in the art.

In various examples, and as depicted in FIG. 1A, PD effluent can flow out of the patient's body 800, through at least one tube 102 and to a drainage bag 105. An imaging chamber 500 can be positioned to receive a fluid sample 108, such as the PD effluent that flows out of the patient's body 800. As will be discussed further, the imaging chamber 500 can include a contrast-enhancing agent and can be configured to mix the fluid sample 108 with the contrast-enhancing agent 521 to form a fluid mixture 556 that can be imaged by an imaging system 400.

In various examples, and as depicted in FIG. 1A, the imaging chamber 500 is in fluid communication with at least one of the tubes 102. For example, the imaging chamber 500 can be positioned on the tube 102 that is coupled to the drainage bag 105. In various examples, and as depicted in FIG. 1A, the imaging chamber 500 can be housed within a collection device 103.

In various examples, and as depicted in FIG. 1B, the imaging chamber 500 can be positioned within the imaging system 400. As such, the PD effluent can flow from the patient's body 800 and into the imaging chamber 500, which is positioned within the imaging system 400.

In various examples, and as depicted in FIG. 1C, the PD effluent can flow into a drainage bag 105. As will be discussed further, the PD effluent can be extracted from the drainage bag 105 and into the imaging chamber 500, which can be inserted into the imaging system 400 to capture image data associated with the PD effluent.

Referring now to FIGS. 2A-2C, an imaging chamber 500 that is configured to receive PD effluent from a drainage bag 105 is depicted, according to an example embodiment. More specifically, FIG. 2A depicts a perspective view of the imaging chamber 500 clamped onto a drainage bag 105, FIG. 2B depicts a top view of the imaging chamber 500, and FIG. 2C depicts a side view of the imaging chamber 500. As depicted in FIG. 2A, the imaging chamber 500 can be configured to clamp onto a periphery of the drainage bag 105. The imaging chamber 500 can include one or more puncturing mechanisms 536, such as needles, to pierce the drainage bag 105 and subsequently fluidly connect the imaging chamber 500 to the drainage bag 105, and allow the PD effluent to flow from the drainage bag 105 and into the imaging chamber 500. In various examples, the imaging chamber 500 receives the flow of the fluid sample 108 through the puncturing mechanisms 536, which can be hollow needles.

As will be explained further, the imaging chamber 500 can include an imaging window 510. The imaging window 510 can be the location that the imaging system 400 images the fluid mixture 556. As depicted in FIG. 2B, the imaging window can be positioned at an extremity of the imaging chamber 500 at a location where the thickness of the imaging chamber 500 is relatively thin.

Referring now to FIGS. 3A-3C, an imaging chamber 500 that is configured to obtain the fluid sample 108, such as PD effluent, from a drainage bag 105 is depicted, according to an example embodiment. More specifically, FIG. 3A depicts a perspective view of the imaging chamber 500 attached to a drainage bag 105, FIG. 3B depicts a top view of the imaging chamber 500, and FIG. 3C depicts a side view of the imaging chamber 500. As depicted in FIG. 3A, the imaging chamber 500 can be configured to puncture a side of the drainage bag 105. The imaging chamber 500 can include one or more puncturing mechanisms 536, such as needles, to fluidly connect the imaging chamber 500 to the drainage bag 105 and allow the fluid sample 108 to flow from the drainage bag 105 and into the imaging chamber 500. In various examples, and as depicted in FIGS. 3B and 3C, the imaging chamber 500 is an assembly that includes a first portion 561 that is configured to adhere to the drainage bag 105 and a second portion 562, which includes the imaging chamber 500, that is removably coupled to the first portion 561. For example, the first portion 561 and the second portion 562 can include threads and the second portion 562, which includes the imaging chamber 500, can be twisted and removed from the first portion 561 that is adhered to the drainage bag 105.

Referring now to FIGS. 4-16, different examples of the imaging chamber 500 are provided. It should be understood that each of the examples provided can be configured to receive a fluid sample 108, such as PD effluent, either from a tube, such as tube 102 that has a flow of the fluid sample 108, or from a drainage bag 105. Additionally, each example of the imaging chamber 500 can be housed within the collection device 103 or positioned within the imaging system 400, and/or coupled to the tube 102 or drainage bag 105. The imaging chamber 500 can be configured to receive a flow of a fluid sample 108, such as a flow of PD effluent, from a patient's body 800, via the tube 102, or from the drainage bag 105. The imaging chamber 500 can include a flow channel 550 that is configured to receive the flow of the fluid sample 108.

Each example of the imaging chamber 500 can be configured to receive the flow of the fluid sample 108 at the end of a tube 102 or configured to receive the flow of the fluid sample 108 in a middle portion of a tube 102 such that the imaging chamber 500 is in-line with the tube 102.

In various examples, the imaging chamber 500 includes a reservoir 520 that is configured to hold a contrast-enhancing agent 521. The contrast-enhancing agent 521 can be a Romanowsky stain, or a sub-type thereof. The contrast-enhancing agent 521 can include eosin, such as eosin Y, oxidized methylene blue, azure B dyes, or combinations thereof. In various examples, the reservoir 520 can be configured to receive the flow of the fluid sample 108.

In various examples, the contrast-enhancing agent 521 is encapsulated to prevent the contrast-enhancing agent 521 from leaking from the reservoir 520. For example, an encapsulation 530 can encapsulate the contrast-enhancing agent 521. In various examples, the imaging chamber 500 includes a seal-breaking mechanism 535 to break the encapsulation 530 of the imaging chamber 500, which can allow the contrast-enhancing agent 521 to mist with the fluid sample 108.

In various examples, once the fluid sample 108 flows inside the imaging chamber 500, via the flow channel 550, and makes contact with the contrast-enhancing agent 521, the imaging chamber 500 can be shaken and/or agitated, either by hand or by a machine, to increase the amount of mixing of the contrast-enhancing agent 521 with the fluid sample 108, which forms a fluid mixture 556. In various examples, the imaging system 400 includes a device to agitate or shake the imaging chamber 500. In various examples, the fluid mixture 556 can flow towards and to an imaging window 510 of the imaging chamber 500 via the flow channel 550. In various examples, the imaging window 510 can be in fluid communication with the reservoir 520 and the imaging window 510 can be downstream from the reservoir 520.

As discussed, the imaging chamber 500 can include an imaging window 510. The imaging window 510 can be configured to be optically clear, or substantially optically clear, such that light can pass through the imaging window 510 while minimizing excess absorption or scattering of the light from the imaging window 510 materials. For example, optical clarity can be defined per testing methods defined in ASTM D-1003. In various examples, the imaging window 510 can comprise glass or a polymer. The imaging chamber 500 can include two imaging windows 510 that are positioned on opposite sides of the imaging chamber 500 so that light can pass through the imaging chamber 500.

In various examples, the reservoir 520 and/or the contrast-enhancing agent 521 is positioned upstream from the imaging window 510 of the imaging chamber 500. In various examples, the flow of the fluid sample 108 passes through the reservoir 520 and/or the contrast-enhancing agent 521, which causes mixing of the fluid sample 108 with the contrast-enhancing agent 521 prior to the fluid sample 108 flowing to the imaging window 510.

In various examples, the imaging chamber 500 includes a flow restriction device that is configured to be at least in an open position and in a closed position. When the flow restriction device is in the open position, the flow restriction device may allow a flow of the fluid sample 108 and/or a flow of the contrast-enhancing agent 521 to flow through and/or past the flow restriction device. When the flow restriction device is in the closed position, the flow restriction device may prevent the flow of the fluid sample 108 and/or the flow of the contrast-enhancing agent 521 to flow through and/or past the flow restriction device.

In various examples, the flow restriction device is a spring-loaded plunger that is actuated (e.g., opened) to release the contrast-enhancing agent 521 and allow the contrast-enhancing agent 521 and/or the fluid sample 108 to flow past and/or through the plunger and allow the contrast-enhancing agent 521 to make contact with the fluid sample 108 and, subsequently, mix with the fluid sample 108. In various examples, the flow restriction device is a valve, such as a ball-valve mechanism, that can be opened to allow the fluid sample 108 and/or the contrast enhancing agent 521 to flow through the valve and allow the contrast-enhancing agent 521 to make contact with the fluid sample 108 and, subsequently, mix with the fluid sample 108.

In various examples, the imaging chamber 500 includes a sensing mechanism that can detect a presence of the fluid sample 108 and can cause the seal-breaking mechanism 535 to break the encapsulation 530. In various examples, the sensing mechanism can detect the presence of the fluid sample 108 and can cause the flow restriction device, such as the ball-valve mechanism or the spring-loaded plunger, to be in the open position.

Figures 4, 5, 6:
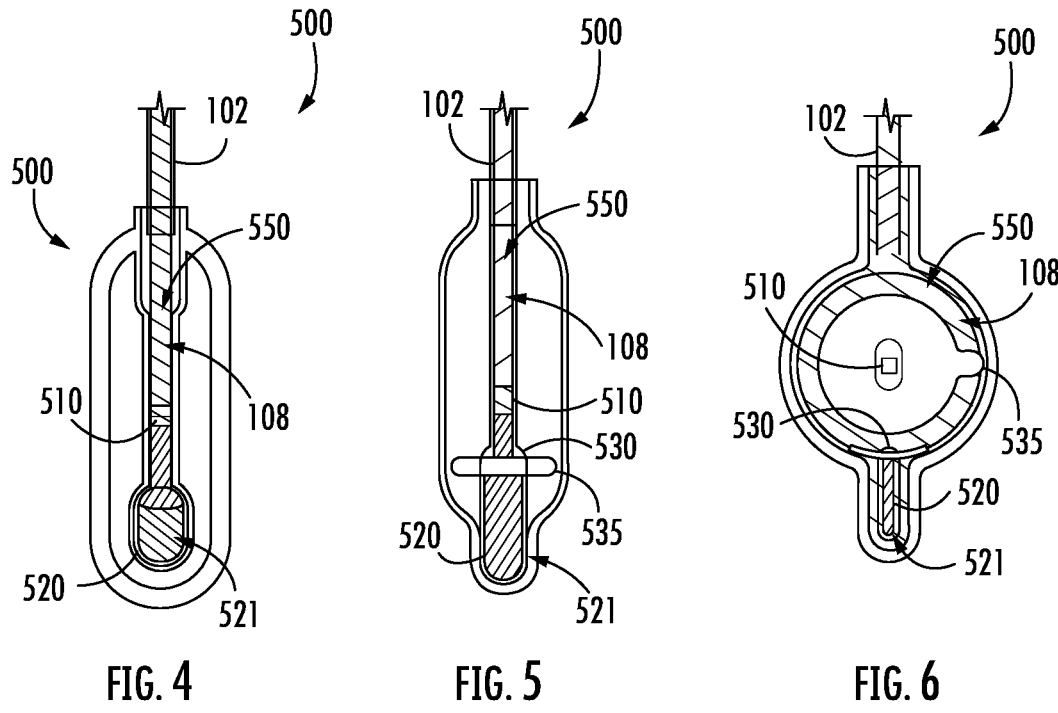

Referring to FIG. 4, a top view of an imaging chamber 500 is provided, in accordance with an example embodiment. In various examples, the imaging chamber 500 may not include an encapsulation 530 or a seal-breaking mechanism 535. Instead, the imaging chamber 500 is configured to receive a flow of the fluid sample 108, which is then allowed to flow towards the contrast-enhancing agent 521 that is within the reservoir 520. Once the fluid sample 108 is within the imaging chamber 500, the imaging chamber 500 can be shaken or agitated to mix the contrast-enhancing agent 521 with the fluid sample 108 to create a fluid mixture 556.

Referring to FIG. 5, a top view of an imaging chamber 500 is provided, in accordance with an example embodiment. In this example, the imaging chamber 500 includes a seal-breaking mechanism 535 that is configured to break the encapsulation 530 that prevents the contrast-enhancing agent 521 from mixing with the fluid sample 108.

Referring to FIG. 6 a top view of an imaging chamber 500 is provided, in accordance with an example embodiment. In this example, the imaging chamber 500 includes a seal-breaking mechanism 535 that is configured to break the encapsulation 530 that prevents the contrast-enhancing agent 521 from mixing with the fluid sample 108. More specifically, the seal-breaking mechanism 535 can be rotated until a tab of the seal-breaking mechanism 535 makes contact with the encapsulation 530 and breaks the encapsulation 530, which can allow the contrast-enhancing agent 521 to mix with the fluid sample 108, forming the fluid mixture 556.

Referring to FIG. 7, a top view of an imaging chamber 500 is provided, in accordance with an example embodiment. In this example, the imaging chamber 500 includes a seal-breaking mechanism 535 that is configured to break the encapsulation 530 that encapsulates the contrast-enhancing agent 521. More specifically, the encapsulation 530 around the contrast-enhancing agent 521 can be pressed, either by hand or by a machine, which increases the fluid pressure of the contrast-enhancing agent 521 within the reservoir 520. The fluid pressure of the contrast-enhancing agent 521 may be sufficiently increased to cause a force great enough to break the encapsulation 530, which can allow the contrast-enhancing agent 521 to mix with the fluid sample 108, forming the fluid mixture 556. In this example, the imaging chamber 500 is configured to receive the flow of the fluid sample 108 at the end of a tube 102.

Referring to FIG. 8, a top view of an imaging chamber 500 is provided, in accordance with an example embodiment. In this example, the imaging chamber 500 includes a seal-breaking mechanism 535 that is configured to break the encapsulation 530 that encapsulates the contrast-enhancing agent 521. More specifically, the seal-breaking mechanism 535 can include a puncturing mechanisms 536, such as a needle, that pierces the encapsulation 530. Additionally, a mixing device 540, such as a helix mixer, can be provided to increase a turbulence of the flow of the fluid sample 108, which may increase the amount of mixing of the contrast-enhancing agent 521 with the fluid sample 108. In this example, the imaging chamber 500 is configured to receive the flow of the fluid sample 108 at the end of a tube 102.

Referring to FIG. 9, a top view of an imaging chamber 500 is provided, in accordance with an example embodiment. In this example, the imaging chamber 500 includes a seal-breaking mechanism 535 that is configured to break the encapsulation 530 that encapsulates the contrast-enhancing agent 521. More specifically, the seal-breaking mechanism 535 can include a puncturing mechanism 536, such as a needle, that pierces the encapsulation 530. Additionally, a mixing device 540, such as a helix mixer, can be provided to increase a turbulence of the flow of the fluid sample 108, which may increase the amount of mixing of the contrast-enhancing agent 521 with the fluid sample 108. In this example, the imaging chamber 500 is configured to receive the flow of the fluid sample 108 in a middle portion of a tube 102. Stated differently, the imaging chamber 500 is in-line with the tube 102.

Referring to FIG. 10, a top view of an imaging chamber 500 is provided, in accordance with an example embodiment. In this example, the imaging chamber 500 does not include a seal-breaking mechanism 535. However, a mixing device 540, such as a helix mixer, is provided to prevent the contrast-enhancing agent 521 from escaping the reservoir 520. Additionally, the mixing device 540 may increase the turbulence of the flow of the fluid sample 108 and may increase the amount of mixing of the contrast-enhancing agent 521 with the fluid sample 108. In this example, the imaging chamber 500 is configured to receive the flow of the fluid sample 108 at the end of a tube 102.

Referring to FIGS. 11A and 111B, a top view of an imaging chamber 500 is provided (FIG. 11A) and a side view of the imaging chamber 500 is provided (FIG. 11B), in accordance with an example embodiment. In this example, the imaging chamber 500 includes a seal-breaking mechanism 535 that is configured to break the encapsulation 530.

More specifically, the seal-breaking mechanism 535 can include a puncturing mechanism 536, such as a needle, that extends from a button 545. The seal-breaking mechanism 535 can be configured to puncture the tube 102 and an encapsulation 530 of the contrast-enhancing agent 521. For example, the imaging chamber 500 can be configured to receive the tube 102 and be snapped onto the tube 102 by pressing down on a button 545 of the imaging chamber 500. Pushing the button 545 can also cause the puncturing mechanism 536 to move towards and puncture the tube 102 and the encapsulation 530 of the contrast-enhancing agent 521. The puncturing mechanism 536 can be hollow and can include one or more inlets that allow the fluid sample 108 to enter the puncturing mechanism 536 and flow to the channel 550. Once the fluid sample 108 is within the channel 550, the fluid sample can mix with the fluid sample 108.

Referring to FIG. 12, a top view of an imaging chamber 500 is provided, in accordance with an example embodiment. In this example, the imaging chamber 500 includes a seal-breaking mechanism 535 that is configured to break the encapsulation 530. More specifically, the seal-breaking mechanism 535 can include a puncturing mechanism 536, such as a needle, that extends from a button 545. The button 545 can be rotatably coupled to the body of the imaging chamber 500 with a hinge 551. The puncturing mechanism 536 can be configured to puncture an encapsulation 530 of the contrast-enhancing agent 521. For example, the imaging chamber 500 can be configured to receive the tube 102 and be snapped onto the tube 102 by pressing down on a button 545 of the imaging chamber 500. Pushing the button 545 can also cause the puncturing mechanism 536 to move towards and puncture the tube 102 and the encapsulation 530 of the contrast-enhancing agent 521. The puncturing mechanism 536 can be hollow and can include one or more inlets that allow the fluid sample 108 to enter the puncturing mechanism 536 and flow to the channel 550. Once the fluid sample 108 is within the channel 550, the fluid sample can mix with the fluid sample 108.

Referring to FIGS. 13A and 13B, a top view of an imaging chamber 500 is provided (FIG. 13A) and a side view of the imaging chamber 500 is provided (FIG. 13B), in accordance with an example embodiment. In this example, the imaging chamber 500 includes a seal-breaking mechanism 535 that is on the bottom of the button 545 and is configured to break the encapsulation 530. More specifically, the seal-breaking mechanism 535 can include a puncturing mechanism 536, such as a needle, that extends from the button 545. The button 545 can be rotatably coupled to the body of the imaging chamber 500 with a hinge 551. The puncturing mechanism 536 can be configured to puncture an encapsulation 530 of the contrast-enhancing agent 521. For example, the imaging chamber 500 can be configured to receive the tube 102 the button 545 can be pushed to cause the puncturing mechanism 536 to move towards and puncture the tube 102 and the encapsulation 530 of the contrast-enhancing agent 521. The puncturing mechanism 536 can be hollow and can include one or more inlets that allow the fluid sample 108 to enter the puncturing mechanism 536 and flow to the channel 550. Once the fluid sample 108 is within the channel 550, the fluid sample can mix with the fluid sample 108, forming the fluid mixture 536.

Referring to FIG. 14, a top view of an imaging chamber 500 is provided, in accordance with an example embodiment. In this example, the imaging chamber 500 includes a seal-breaking mechanism 535 (not shown) that is configured to break the encapsulation 530. The seal breaking mechanism 535 of FIG. 14 can operate the same as or similarly to the seal breaking mechanism 535 of FIGS. 13A and 13B.

In various examples, and as depicted in FIG. 14, the imaging chamber 500 can be housed within a collection device 103. Incorporating the imaging chamber 500 within a collection device 103 can increase the ease of handling the imaging chamber 500 because the imaging chamber 500 may be relatively small. Also, in this example, the imaging chamber 500 is configured to be in line with the tube 102.

Referring to FIG. 15, a top view of an imaging chamber 500 is provided, in accordance with an example embodiment. In this example, the imaging chamber 500 includes a seal-breaking mechanism 535 (not shown) that is configured to break the encapsulation 530. The seal breaking mechanism 535 of FIG. 14 can operate the same as or similarly to the seal breaking mechanism 535 of FIGS. 13A and 13B.

Referring to FIG. 16, a top view of an imaging chamber 500 is provided, in accordance with an example embodiment. In this example, the imaging chamber 500 does not include a seal-breaking mechanism 535 that is configured to break the encapsulation 530. Instead, the fluid sample 108 flows towards and through the reservoir 520 that stores the contrast-enhancing agent 521. As the fluid sample 108 flows through the reservoir 520, the fluid sample 108 mixes with the contrast-enhancing agent 521, forming the fluid mixture 556. The fluid mixture 556 then flows towards the imaging window 510, which is positioned downstream from the reservoir 520.

Referring to FIG. 17, a schematic representation of an imaging system 400 is provided, in accordance with an example embodiment. In various examples, and as shown in the example of FIG. 17, the imaging system 400 includes an illumination device 402 and an imaging device 406. The imaging system 400 can be configured to receive an imaging chamber 500.

As discussed, the imaging chamber 500 can include an imaging window 510 that can be optically clear, or substantially optically clear. For example, the imaging window 510 can comprise a transparent, or substantially transparent, material, such as glass or a clear polymer.

In various examples, the imaging chamber 500 may define a hollow portion that forms the flow channel 550. For example, the flow channel 550 within the imaging chamber 500 may be in the form of a cavity that is between an upper substrate 509 and a lower substrate 511. In some embodiments, the flow channel 550 provides a passageway for a fluid mixture 556 to flow inside the imaging chamber 500 and to the imaging window 510. In various examples, the imaging chamber 500 is removable or replaceable. For example, the imaging chamber 500 may be removed from the imaging system 400 and replaced after each use.

As discussed, the fluid mixture 556 can include a fluid sample 108, such as a PD effluent, and a contrast-enhancing agent 521. In various other examples, the fluid mixture 556 may comprise additional or alternative fluid samples other than the PD effluent. For example, the fluid mixture 556 can include urine. Additionally, or alternatively, the fluid sample 108 can include oil. Additionally, or alternatively, the fluid sample 108 can include blood. Additionally, or alternatively, the fluid sample 108 can include joint fluid.

As discussed, the imaging system 400 can include an illumination device 402. The illumination device 402 can be configured to produce, generate, emit, and/or trigger the production, generation, and/or emission of light. The example illumination device 402 may include, but is not limited to, laser diodes (for example, UV, visible, or IR laser diodes, edge-emitting laser diodes, surface-emitting laser diodes, and/or the like). Additionally, or alternatively, the illumination device 402 may comprise one or more light-emitting diodes (LEDs). Additionally, or alternatively, the illumination device 402 may comprise one or more other forms of natural and/or artificial sources of light.

In some embodiments, at least one illumination device 402 is configured to emit at least one light beam. In some embodiments, the at least one light beam emitted by the at least one illumination device 402 may comprise coherent light. In the present disclosure, the term "coherent light" refers to a light beam where the wavefront has a synchronized phase. Examples of coherent light include, but are not limited to, laser light. For example, the light beam in laser light has the same frequency and phase. In some embodiments, to emit coherent light, the at least one illumination device 402 includes, but is not limited to, laser diodes (for example, UV, visible, or IR laser diodes, edge-emitting laser diodes, surface-emitting laser diodes, and/or the like).

In some embodiments, the at least one light beam emitted by the at least one illumination device 402 may comprise incoherent light or at least partially incoherent light. In the present disclosure, the term "incoherent light" (or "low coherence light" as used interchangeably herein) refers to a light beam where the wavefront does not have a synchronized phase. For example, incoherent light does not contain photons with the same frequency and does not have wavelengths that are in phase with one another. In some embodiments, to emit incoherent light, the at least one illumination device 402 includes, but is not limited to, light-emitting diodes (LEDs) or lamps.

In various examples, the illumination device 402 is positioned above the imaging chamber 500. For example, the illumination device 402 can be positioned above and aligned with the imaging window 510 of the imaging chamber 500. At least one light beam emitted by the illumination device 402 can be directed to a top surface of the imaging chamber 500. The at least one light beam can pass through the imaging window 510 and through the fluid mixture 556 that is within the flow channel 550 of the imaging chamber 500. The at least one light beam can also pass through the lower substrate 511 and to the imaging device 406 that is positioned under the imaging chamber 500.

In various examples, the imaging device 406 includes an image sensor that generates digital holography image data associated with the fluid mixture 556 in the flow channel 550 of the imaging chamber 500. In the present disclosure, the term "digital holography image data" refers to image data that is generated based on digital holography techniques, including, but not limited to, lensless holography techniques. For example, the digital holography image data may be generated by the image sensor without any imaging lenses and without any adjustments, such as optomechanical focusing adjustments. In such an example, there are no imaging lenses between the bottom surface of the imaging chamber 500 and the image sensor. The digital holography image data may comprise a digital holography image of the fluid mixture 556 (for example, a digital holography image of various particles, cells, etc. in the fluid mixture 556).

In some examples, the image sensor may comprise one or more imagers and/or image sensors. Various examples of the image sensor may include, but are not limited to, a charge-coupled device (CCD), a complementary metal-oxide semiconductor (CMOS) sensor, and/or the like. As described above, in some embodiments, the image sensor does not comprise any lenses so as to generate digital holography image data based on lensless holography techniques.

While the description above provides an example of implementing digital holography techniques, it is noted that the scope of the present disclosure is not limited to the description above. In some examples, an example fluid sample 108 imaging system 400 may implement other imaging techniques. For example, example embodiments of the present disclosure may implement optical microscopy as the imaging technique. Additionally, or alternatively, example embodiments of the present disclosure may implement ultraviolet (UV) fluorescence as the imaging technique.

While the description above provides an example positional arrangement between the illumination device 402 and the imaging chamber 500 and an example positional arrangement between the imaging chamber 500 and the imaging device 406, it is noted that the scope of the present disclosure is not limited to the description above. In some examples, the illumination device 402, the imaging chamber 500, and/or the imaging device 406 of an example imaging system 400 may be positioned differently than those shown in FIG. 17. For example, the illumination device 402 may be positioned under the imaging chamber 500, and the imaging device 406 may be positioned above the imaging chamber 500.

Referring now to FIG. 18, a flowchart of a method 900 for imaging a fluid mixture 556 with an imaging system 400 is depicted, according to an example embodiment. The method can include a step 910 of receiving a fluid sample 108, such as PD effluent, that comprises biological cells, such as red blood cells and/or white blood cells, into an imaging chamber 500. The imaging chamber 500 can include a contrast-enhancing agent 521. For example, the imaging chamber 500 can include the contrast-enhancing agent 521 prior to the imaging chamber 500 receives the fluid sample 108.

The method 900 can include a step 920 of mixing the fluid sample 108 with the contrast-enhancing agent 521 to form the fluid mixture 556. For example, the imaging chamber 500 can be shaken or agitated by hand or by machine. In various examples, the imaging chamber 500 can include a mixing device 540 to increase the turbulence of the flow of the fluid sample 108, which may increase the mixing of the fluid sample 108 with the contrast-enhancing agent 521. The step 920 of mixing the fluid sample 108 with the contest-enhancing agent 521 can be done outside of an imaging system 400, by hand or by machine, or within the imaging system 400, by machine. In various examples, the imaging system 400 includes an agitation device to shake or agitate the imaging chamber 500.

The method 900 can include a step 930 of imaging the fluid mixture 556 that is within the imaging chamber 500 with the imaging system 400. For example, an imaging device 406, in conjunction with an illumination device 402, can image the fluid mixture 556.

Conclusion

The above descriptions of various embodiments of the subject disclosure and corresponding figures and what is described in the Abstract, are described herein for illustrative purposes, and are not intended to be exhaustive or to limit the disclosed embodiments to the precise forms disclosed. It is to be understood that one of ordinary skill in the art may recognize that other embodiments having modifications, permutations, combinations, and additions can be implemented for performing the same, similar, alternative, or substitute functions of the disclosed subject matter, and are therefore considered within the scope of this disclosure.

Therefore, the disclosed subject matter should not be limited to any single embodiment described herein, but rather should be construed in breadth and scope in accordance with the appended claims below. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An imaging chamber configured to receive a flow of a fluid sample, the imaging chamber comprising:
    a reservoir comprising:
        a contrast-enhancing agent, wherein the contrast-enhancing agent is encapsulated within an encapsulation of the reservoir, the reservoir configured to receive the flow of the fluid sample; and
        a mixing device comprised within the reservoir, wherein the mixing device facilitates mixing of the flow of the fluid sample with the contrast-enhancing agent to form a fluid mixture;
    a seal-breaking mechanism configured to break the encapsulation of the reservoir to release the contrast-enhancing agent for mixing with the fluid sample; and
    an imaging window in fluid communication with the reservoir to receive the fluid mixture from the reservoir, wherein the imaging window is downstream from the reservoir, wherein the fluid mixture flows towards the imaging window from the reservoir and the fluid mixture is imaged by an imaging system.

2. The imaging chamber of claim 1, wherein the imaging window is optically clear, wherein the imaging chamber is configured to be imaged by the imaging system, and wherein the imaging system comprises an illumination device and an imaging device.

3. The imaging chamber of claim 1, further comprising a flow restriction device that is configured to be in an open position and in a closed position, wherein the flow restriction device is configured to allow a flow of the fluid sample and/or a flow of the contrast-enhancing agent to flow through and/or past the flow restriction device when the flow restriction device is in the open position, and wherein the flow restriction device is configured to prevent the flow of the fluid sample and/or the flow of the contrast-enhancing agent to flow through and/or past the flow restriction device when the flow restriction device is in the closed position.

4. The imaging chamber of claim 1, wherein the seal-breaking mechanism is further configured to puncture a tube that comprises the flow of the fluid sample.

5. The imaging chamber of claim 4, wherein the fluid sample is a peritoneal dialysis effluent.

6. The imaging chamber of claim 1, further comprising a puncturing mechanism that is configured to pierce a drainage bag or tube, wherein the imaging chamber receives the flow of the fluid sample through the puncturing mechanism.

7. An imaging system configured to receive an imaging chamber, wherein the imaging system comprises:
    an illumination device; and
    an imaging device, wherein the imaging system is configured to receive the imaging chamber between the illumination device and the imaging device, wherein the imaging chamber comprises:

a reservoir comprising a contrast-enhancing agent, wherein the contrast-enhancing agent is encapsulated within an encapsulation of the reservoir, the reservoir is configured to receive a flow of a fluid sample;

a mixing device comprised within the reservoir, wherein the mixing device facilitates mixing of the flow of the fluid sample with the contrast-enhancing agent to form a fluid mixture;

a seal-breaking mechanism configured to break the encapsulation of the reservoir to release the contrast-enhancing agent for mixing with the fluid sample; and an imaging window in fluid communication with the reservoir to receive the fluid mixture from the reservoir, wherein the imaging window is downstream from the reservoir to receive the fluid mixture from the reservoir flows towards the imaging window from the reservoir wherein the fluid mixture is imaged by the imaging system, and wherein the imaging device is configured to be aligned with the imaging window of the imaging chamber.

8. The imaging system of claim 7, wherein the imaging system comprises an agitation device that is configured to agitate or shake the imaging chamber.

9. The imaging system of claim 7, wherein the imaging system is configured to receive the flow of the fluid sample and the imaging chamber is configured to be within the imaging system when it receives the flow of the fluid sample.

10. A method for imaging a fluid mixture with an imaging system, the method comprising:

receiving, by an imaging chamber, a flow of a fluid sample, wherein the imaging chamber comprises a reservoir and an imaging window;

mixing, within the reservoir, the flow of the fluid sample with a contrast-enhancing agent to form a fluid mixture, wherein the reservoir comprises of the contrast-enhancing agent, wherein the contrast-enhancing agent is encapsulated within an encapsulation of the reservoir, the reservoir is configured to receive a flow of a fluid sample;

configuring a seal-breaking mechanism to break the encapsulation of the reservoir and to release the contrast-enhancing agent for mixing with the fluid sample;

receiving, by the imaging window, the fluid mixture, wherein the imaging window is in fluidic communication with the reservoir, wherein the imaging window is downstream from the reservoir, wherein the fluid mixture flows towards the imaging window from the reservoir; and imaging, by the imaging system, the fluid mixture.

11. The method of claim 10, wherein receiving the fluid sample comprises receiving the fluid sample from a bag or tube.

12. The method of claim 10, further comprising opening a flow restriction device of the imaging chamber.

13. The method of claim 10, wherein mixing the fluid sample with the contrast-enhancing agent comprises mixing the fluid sample with the contrast-enhancing agent with a mixing device.

14. The method of claim 10, wherein the fluid sample comprises a PD effluent.

15. The method of claim 10, wherein the imaging system comprises a digital holography imaging device.

16. The method of claim 10, wherein mixing the fluid sample with the contrast-enhancing agent is performed by hand outside of the imaging system.

17. The method of claim 10, wherein mixing the fluid sample with the contrast-enhancing agent is performed inside the imaging system by an agitation device of the imaging system.

* * * * *